(12) United States Patent
Braun et al.

(10) Patent No.: US 8,332,982 B2
(45) Date of Patent: Dec. 18, 2012

(54) VIBRATING TOOTHBRUSH

(75) Inventors: Phillip M Braun, Exeter, RI (US);
Joseph Syndosis, Wayland, MA (US);
Ronald R Duff, Jr., Shrewsbury, MA
(US); Richard H. Cohen, Sherborn, MA
(US); Thomas Craig Masterman,
Brookline, MA (US)

(73) Assignee: The Gillette Company, Boston, MA (US)

( * ) Notice: Subject to any disclaimer, the term of this patent is extended or adjusted under 35 U.S.C. 154(b) by 80 days.

(21) Appl. No.: 12/546,066

(22) Filed: Aug. 24, 2009

(65) Prior Publication Data
US 2010/0162499 A1 Jul. 1, 2010

Related U.S. Application Data

(63) Continuation of application No. 10/830,693, filed on Apr. 23, 2004, now abandoned.

(51) Int. Cl.
*A46B 9/04* (2006.01)
(52) U.S. Cl. ............... 15/22.1; 15/167.1; 15/110
(58) Field of Classification Search .......... 15/22.1, 15/167.1, 110, 207.2
See application file for complete search history.

(56) References Cited

U.S. PATENT DOCUMENTS

| | | |
|---|---|---|
| 301,644 A | 7/1884 | Thompson |
| 429,839 A | 6/1890 | Beissbarth |
| 601,405 A | 3/1898 | Shepherd |
| 819,444 A | 5/1906 | Monroe |
| 1,022,920 A | 4/1912 | Anderson |
| 1,063,523 A | 6/1913 | Farrar |
| 1,128,139 A | 2/1915 | Hoffman |
| 1,142,698 A | 6/1915 | Grove et al. |
| 1,172,109 A | 2/1916 | Cammack |
| 1,191,556 A | 7/1916 | Blake |
| 1,268,544 A | 12/1916 | Cates |
| 1,251,250 A | 12/1917 | Libby |
| 1,323,042 A | 11/1919 | Gardner |

(Continued)

FOREIGN PATENT DOCUMENTS

AU B44696/93 8/1993

(Continued)

OTHER PUBLICATIONS

Computer generated English translation of DE 3628722 A1, Weihrauch, Feb. 1988.*

(Continued)

*Primary Examiner* — Laura C Guidotti
(74) *Attorney, Agent, or Firm* — David M. Weirich; George H. Leal

(57) ABSTRACT

A toothbrush has a head extending from a neck which extends from a handle, and the head has a plurality of tooth cleaning elements extending therefrom. A first group of tooth cleaning elements is located towards a free end of the head, and a second group of tooth cleaning elements is located towards the outside of the head. A third group of tooth cleaning elements, which alternate with the second group of tufts, are oriented at an acute angle to a top surface of the head in a direction that is across the width of the head. A fourth group of tooth cleaning elements is located toward the inside of the head, and each is made of a thermoplastic elastomer and each is in the shape of a curved wall. A fifth group of tooth cleaning elements is located towards the inside of the head.

25 Claims, 13 Drawing Sheets

U.S. PATENT DOCUMENTS

| | | |
|---|---|---|
| 1,390,973 A | 9/1921 | Niessen Ernst Hermann Wilhelm Von |
| 1,526,267 A | 9/1924 | Dessau |
| 1,673,638 A | 6/1928 | Peterson |
| 1,683,866 A | 9/1928 | Chandler |
| 1,693,229 A | 11/1928 | Felmar |
| 1,698,128 A | 1/1929 | Funk |
| 1,704,564 A | 3/1929 | Friedland |
| 1,753,290 A | 4/1930 | Graves |
| 1,758,632 A | 5/1930 | Wagner |
| 1,764,130 A | 6/1930 | Vardeman |
| 1,796,893 A | 3/1931 | McVeigh |
| 1,797,946 A | 3/1931 | Eichel |
| 1,863,389 A | 5/1931 | Anderson |
| 1,840,246 A | 1/1932 | Newman |
| 1,908,510 A | 5/1933 | Dodson |
| 1,924,152 A | 8/1933 | Coney et al. |
| 1,946,283 A | 2/1934 | Hoffman et al. |
| 1,963,389 A | 6/1934 | Vardeman |
| 1,993,662 A | 3/1935 | Green |
| 2,042,239 A | 5/1936 | Planding |
| 2,155,473 A | 9/1936 | Coleman |
| 2,088,839 A | 8/1937 | Coney et al. |
| 2,117,174 A | 5/1938 | Jones |
| 2,129,082 A | 9/1938 | Byrer |
| 2,139,245 A | 12/1938 | Ogden |
| 2,154,846 A | 4/1939 | Heymann et al. |
| 2,164,219 A | 6/1939 | McGerry |
| 2,172,624 A | 9/1939 | Gabriel et al. |
| 2,176,309 A | 10/1939 | Love et al. |
| 2,189,175 A | 2/1940 | Jackson |
| 2,206,726 A | 7/1940 | Lasater |
| 2,219,753 A | 10/1940 | Seguin |
| 2,225,331 A | 12/1940 | Campbell |
| 2,238,603 A | 4/1941 | Runnels |
| 2,244,699 A | 6/1941 | Hosey |
| 2,246,867 A | 6/1941 | Thomas et al. |
| 2,263,802 A | 11/1941 | Grusin |
| 2,266,195 A | 12/1941 | Lay |
| 2,279,355 A | 4/1942 | Wilensky |
| 2,312,828 A | 3/1943 | Adamsson |
| 2,326,632 A | 8/1943 | Friedman |
| 2,328,998 A | 9/1943 | Radford |
| 2,364,205 A | 12/1944 | Fuller |
| 2,486,203 A | 10/1949 | Pieper |
| 2,486,847 A | 11/1949 | Hokett |
| 2,556,691 A | 6/1951 | Harshbarger |
| 2,604,649 A | 7/1952 | Stephenson et al. |
| 2,637,870 A | 5/1953 | Cohen |
| 2,702,914 A | 3/1955 | Kittle et al. |
| 2,832,088 A | 4/1958 | Peilet et al. |
| 2,882,544 A | 4/1959 | Hadidian |
| 2,935,755 A | 5/1960 | Leira et al. |
| 3,007,441 A | 11/1961 | Eyer |
| 3,016,554 A | 1/1962 | Peterson |
| 3,050,072 A | 8/1962 | Diener |
| 3,103,027 A | 9/1963 | Birch |
| 3,110,918 A | 11/1963 | Tate, Jr. |
| 3,128,487 A | 4/1964 | Vallis |
| 3,129,449 A | 4/1964 | Cyzer |
| 3,159,859 A | 12/1964 | Rasmussen |
| 3,177,509 A | 4/1965 | Cyzer |
| 3,230,562 A | 1/1966 | Birch |
| 3,258,805 A | 7/1966 | Rossnan |
| 3,295,156 A | 1/1967 | Brant |
| 3,302,230 A | 2/1967 | Poppelman |
| 3,316,576 A | 5/1967 | Urbush |
| 3,327,339 A | 6/1967 | Lemelson |
| 3,359,588 A | 12/1967 | Kobler |
| 3,398,421 A | 8/1968 | Rashbaum |
| 3,403,070 A | 9/1968 | Lewis, Jr. |
| 3,411,979 A | 11/1968 | Lewis |
| RE26,688 E | 10/1969 | Lemelson |
| 3,553,759 A | 1/1971 | Kramer et al. |
| 3,613,143 A | 10/1971 | Muhler et al. |
| 4,033,008 A | 7/1977 | Warren et al. |
| 4,081,877 A | 4/1978 | Vitale |
| 4,114,222 A | 9/1978 | Serediuk |
| 4,128,910 A | 12/1978 | Nakata et al. |
| 4,156,620 A | 5/1979 | Clemens |
| 4,167,794 A | 9/1979 | Pomeroy |
| 4,202,361 A | 5/1980 | Bills |
| 4,263,691 A | 4/1981 | Pakarnseree |
| 4,277,862 A | 7/1981 | Weideman |
| 4,288,883 A | 9/1981 | Dolinsky |
| 4,356,585 A | 11/1982 | Protell et al. |
| 4,373,541 A | 2/1983 | Nishioka |
| 4,391,951 A | 7/1983 | Scheetz |
| 4,403,623 A | 9/1983 | Mark |
| 4,409,701 A | 10/1983 | Perches |
| 4,429,434 A | 2/1984 | Sung-Shan |
| 4,438,541 A | 3/1984 | Jacob et al. |
| 4,462,136 A | 7/1984 | Nakao et al. |
| 4,472,853 A | 9/1984 | Rauch |
| 4,475,261 A | 10/1984 | Okumura et al. |
| 4,476,280 A | 10/1984 | Poppe et al. |
| 4,480,351 A | 11/1984 | Koffler |
| 4,517,701 A | 5/1985 | Stanford, Jr. |
| 4,525,531 A | 6/1985 | Zukosky et al. |
| 4,534,081 A | 8/1985 | Spademan |
| 4,545,087 A | 10/1985 | Nahum |
| 4,585,416 A | 4/1986 | DeNiro et al. |
| 4,603,166 A | 7/1986 | Poppe et al. |
| 4,616,064 A | 10/1986 | Zukosky et al. |
| 4,616,374 A | 10/1986 | Novogrodsky |
| 4,617,342 A | 10/1986 | Poppe et al. |
| 4,617,694 A | 10/1986 | Bori |
| 4,623,495 A | 11/1986 | Degoix et al. |
| 4,633,542 A | 1/1987 | Taravel |
| 4,654,922 A | 4/1987 | Chen |
| 4,672,706 A | 6/1987 | Hill |
| 4,691,405 A | 9/1987 | Reed |
| 4,694,844 A | 9/1987 | Berl et al. |
| 4,706,322 A | 11/1987 | Nicolas |
| 4,724,569 A | 2/1988 | Eguchi et al. |
| 4,751,761 A | 6/1988 | Breitschmid |
| 4,751,768 A | 6/1988 | Trujillo, Sr. |
| 4,776,054 A | 10/1988 | Rauch |
| 4,783,874 A | 11/1988 | Perches et al. |
| 4,802,255 A | 2/1989 | Breuer et al. |
| 4,833,194 A | 5/1989 | Kuan et al. |
| 4,845,795 A | 7/1989 | Crawford et al. |
| 4,852,202 A | 8/1989 | Ledwitz |
| 4,882,803 A | 11/1989 | Rogers et al. |
| 4,892,698 A | 1/1990 | Weihrauch |
| 4,894,880 A | 1/1990 | Aznavoorian |
| 4,913,133 A | 4/1990 | Tichy |
| 4,958,402 A | 9/1990 | Weihrauch |
| 4,979,782 A | 12/1990 | Weihrauch |
| 4,989,287 A | 2/1991 | Scherer |
| 4,991,249 A | 2/1991 | Suroff |
| 5,020,179 A | 6/1991 | Scherer |
| 5,021,475 A | 6/1991 | Isayev |
| 5,034,450 A | 7/1991 | Betz et al. |
| 5,040,260 A | 8/1991 | Michaels |
| 5,046,213 A * | 9/1991 | Curtis et al. .................. 15/167.1 |
| D325,821 S | 5/1992 | Schwartz |
| 5,114,214 A | 5/1992 | Barman |
| 5,120,225 A | 6/1992 | Amit |
| 5,137,039 A | 8/1992 | Klinkhammer |
| 5,142,724 A | 9/1992 | Park |
| 5,165,131 A | 11/1992 | Staar |
| 5,184,368 A | 2/1993 | Holland |
| 5,186,627 A | 2/1993 | Amit et al. |
| 5,228,166 A | 7/1993 | Gomez |
| 5,269,038 A | 12/1993 | Bradley |
| D345,054 S | 3/1994 | Spence, Jr. |
| 5,291,878 A | 3/1994 | Lombardo et al. |
| 5,313,909 A | 5/1994 | Tseng et al. |
| 5,318,352 A | 6/1994 | Holland |
| 5,321,726 A | 6/1994 | Kafadar |
| 5,325,560 A | 7/1994 | Pavone et al. |
| 5,334,646 A | 8/1994 | Chen |
| D350,851 S | 9/1994 | Spence, Jr. |
| 5,350,248 A | 9/1994 | Chen |
| 5,357,644 A | 10/1994 | Theriault |

| | | | | | | |
|---|---|---|---|---|---|---|
| 5,392,483 | A | 2/1995 | Heinzelman et al. | 6,209,164 B1 | 4/2001 | Sato |
| 5,398,366 | A | 3/1995 | Bradley | D443,985 S | 6/2001 | Beals et al. |
| 5,407,254 | A | 4/1995 | Hegemann | 6,253,404 B1 | 7/2001 | Boland et al. |
| 5,421,726 | A | 6/1995 | Okada | 6,269,514 B1 | 8/2001 | Edwards et al. |
| 5,435,032 | A | 7/1995 | McDougall | D448,171 S | 9/2001 | Harris et al. |
| 5,458,400 | A | 10/1995 | Meyer | D448,172 S | 9/2001 | Harris et al. |
| 5,476,384 | A | 12/1995 | Giuliani et al. | D448,173 S | 9/2001 | Harris et al. |
| 5,500,975 | A | 3/1996 | Sano | 6,283,751 B1 | 9/2001 | White |
| D368,803 | S | 4/1996 | Yost et al. | 6,286,173 B1 | 9/2001 | Briones |
| D368,804 | S | 4/1996 | Yost et al. | 6,290,302 B1 | 9/2001 | Boucherie |
| 5,524,319 | A | 6/1996 | Avidor | 6,290,303 B1 | 9/2001 | Boucherie |
| 5,528,786 | A | 6/1996 | Porat et al. | 6,298,516 B1 | 10/2001 | Beals et al. |
| 5,533,227 | A * | 7/1996 | Ito et al. ............... 15/167.1 | 6,308,367 B1 | 10/2001 | Beals et al. |
| 5,535,474 | A | 7/1996 | Salazar | 6,351,868 B1 | 3/2002 | Edwards et al. |
| D372,584 | S | 8/1996 | Yost et al. | 6,363,565 B1 | 4/2002 | Paffrath |
| 5,546,626 | A | 8/1996 | Chung | 6,389,634 B1 | 5/2002 | Devlin et al. |
| D373,681 | S | 9/1996 | Yost et al. | 6,391,445 B1 | 5/2002 | Weihrach |
| D374,122 | S | 10/1996 | Yost et al. | 6,405,401 B1 | 6/2002 | Hellerud et al. |
| D374,350 | S | 10/1996 | Yost et al. | 6,421,865 B1 | 7/2002 | McDougall |
| D374,775 | S | 10/1996 | Yost et al. | 6,421,867 B1 | 7/2002 | Weihrauch |
| 5,590,434 | A | 1/1997 | Imai | 6,453,497 B1 | 9/2002 | Chiang et al. |
| 5,593,213 | A | 1/1997 | Meessmann | 6,463,618 B1 | 10/2002 | Zimmer |
| 5,604,951 | A | 2/1997 | Shipp | 6,477,729 B1 | 11/2002 | Ben-Ari |
| 5,628,082 | A | 5/1997 | Moskovich | 6,513,182 B1 | 2/2003 | Calebrese et al. |
| 5,651,157 | A | 7/1997 | Hahn | 6,543,083 B1 | 4/2003 | Edwards |
| 5,678,275 | A | 10/1997 | Derfner | 6,553,604 B1 | 4/2003 | Braun et al. |
| D386,617 | S | 11/1997 | Shyu | 6,564,416 B1 | 5/2003 | Claire et al. |
| 5,706,542 | A | 1/1998 | Okaka | 6,571,417 B1 | 6/2003 | Gavney, Jr. et al. |
| 5,722,106 | A | 3/1998 | Masterman et al. | 6,601,257 B1 | 8/2003 | Felix-Flender et al. |
| 5,723,543 | A | 3/1998 | Modic | 6,658,688 B2 | 12/2003 | Gavney, Jr. |
| 5,735,011 | A | 4/1998 | Asher | 6,701,565 B2 | 3/2004 | Hafemann |
| 5,778,474 | A | 7/1998 | Shek | 6,725,490 B2 | 4/2004 | Blaustein et al. |
| 5,791,007 | A | 8/1998 | Tsai | 6,732,398 B2 | 5/2004 | McConnell |
| 5,799,354 | A | 9/1998 | Amir | 6,764,142 B2 | 7/2004 | Kwon |
| 5,802,656 | A | 9/1998 | Dawson et al. | 6,776,597 B2 | 8/2004 | Buhler |
| 5,813,079 | A | 9/1998 | Halm | 6,805,557 B2 | 10/2004 | Davies et al. |
| 5,823,633 | A | 10/1998 | Weihrauch | 6,807,703 B2 | 10/2004 | Van Gelder et al. |
| D401,414 | S | 11/1998 | Vrignaud | 6,820,300 B2 | 11/2004 | Gavney, Jr. |
| 5,836,033 | A | 11/1998 | Berge | 6,826,797 B2 | 12/2004 | Chenvainu et al. |
| 5,839,148 | A | 11/1998 | Volpenhein | 6,859,969 B2 | 3/2005 | Gavney, Jr. et al. |
| D402,114 | S | 12/1998 | Fleming et al. | 6,865,767 B1 | 3/2005 | Gavney, Jr. |
| D402,116 | S | 12/1998 | Magloff et al. | 6,889,401 B2 | 5/2005 | Fattori et al. |
| D402,117 | S | 12/1998 | Fleming et al. | 6,892,412 B2 | 5/2005 | Gatzemeyer et al. |
| 5,842,249 | A | 12/1998 | Sato | 6,892,413 B2 | 5/2005 | Blaustein et al. |
| D403,510 | S | 1/1999 | Menke et al. | 6,918,154 B2 | 7/2005 | Ben-Ari |
| 5,864,915 | A | 2/1999 | Ra | 6,931,688 B2 | 8/2005 | Moskovich et al. |
| D406,464 | S | 3/1999 | Yost et al. | 6,938,294 B2 | 9/2005 | Fattori et al. |
| 5,892,412 | A | 4/1999 | Norte et al. | 6,966,093 B2 | 11/2005 | Eliav et al. |
| 5,896,614 | A | 4/1999 | Flewitt | 6,983,507 B2 | 1/2006 | McDougall |
| 5,930,860 | A | 8/1999 | Shipp | 6,988,777 B2 | 1/2006 | Pfenniger et al. |
| 5,930,861 | A | 8/1999 | White | 6,993,804 B1 | 2/2006 | Braun et al. |
| 5,946,759 | A | 9/1999 | Cann | 7,008,225 B2 | 3/2006 | Ito et al. |
| 5,946,789 | A | 9/1999 | Junkers | 7,014,800 B2 | 3/2006 | Weihrauch |
| 5,970,564 | A | 10/1999 | Inns et al. | 7,137,163 B2 | 11/2006 | Gatzemeyer et al. |
| 5,974,619 | A | 11/1999 | Weihrach | 7,160,508 B2 | 1/2007 | Lee |
| 5,987,681 | A | 11/1999 | Hahn et al. | 7,251,849 B2 | 8/2007 | Moskovich |
| 5,987,688 | A | 11/1999 | Roberts et al. | 7,392,562 B2 | 7/2008 | Boland et al. |
| 5,991,959 | A | 11/1999 | Raven et al. | 2001/0007161 A1 | 7/2001 | Masterman et al. |
| 6,018,840 | A | 2/2000 | Guay et al. | 2001/0020314 A1 | 9/2001 | Calabrese |
| 6,021,541 | A | 2/2000 | Mori et al. | 2002/0004964 A1 | 1/2002 | Luchino et al. |
| 6,035,476 | A | 3/2000 | Underwood et al. | 2002/0084550 A1 | 7/2002 | Roberts et al. |
| 6,044,514 | A | 4/2000 | Kaneda et al. | 2002/0092109 A1 | 7/2002 | Edwards et al. |
| 6,058,541 | A | 5/2000 | Masterman et al. | 2002/0116778 A1 | 8/2002 | Kwon |
| 6,067,684 | A | 5/2000 | Kweon | 2002/0124333 A1 * | 9/2002 | Hafliger et al. ............... 15/22.1 |
| 6,088,869 | A | 7/2000 | Kaneda et al. | 2002/0192621 A1 | 12/2002 | Ben-Ari |
| 6,088,870 | A | 7/2000 | Hohlbein | 2003/0033680 A1 | 2/2003 | Davies et al. |
| 6,090,488 | A | 7/2000 | Kweon | 2003/0033682 A1 | 2/2003 | Davies et al. |
| 6,096,151 | A | 8/2000 | Edwards et al. | 2003/0041402 A1 | 3/2003 | Stein |
| D430,730 | S | 9/2000 | Klein | 2003/0066147 A1 | 4/2003 | Roh |
| 6,112,361 | A | 9/2000 | Brice | 2003/0077107 A1 | 4/2003 | Kuo |
| 6,138,310 | A | 10/2000 | Porper et al. | 2003/0079304 A1 | 5/2003 | Dworzen |
| 6,151,745 | A | 11/2000 | Roberts et al. | 2003/0084525 A1 | 5/2003 | Blaustein |
| 6,161,243 | A | 12/2000 | Weihrauch | 2003/0084528 A1 | 5/2003 | Chan |
| 6,161,245 | A | 12/2000 | Weihrauch | 2003/0088932 A1 | 5/2003 | Gardiner |
| D436,733 | S | 1/2001 | Klein | 2003/0115701 A1 | 6/2003 | Edwards |
| 6,178,582 | B1 | 1/2001 | Halm | 2003/0115702 A1 | 6/2003 | Edwards |
| 6,199,242 | B1 | 3/2001 | Masterman et al. | 2003/0115703 A1 | 6/2003 | Edwards |
| 6,202,241 | B1 | 3/2001 | Hassell et al. | 2003/0115707 A1 | 6/2003 | Buford |
| D440,048 | S | 4/2001 | Beals et al. | 2003/0140440 A1 | 7/2003 | Gavney, Jr. |

| | | | | | | |
|---|---|---|---|---|---|---|
| 2003/0159224 A1 | 8/2003 | Fischer et al. | EP | 0 783 850 B1 | 3/2001 | |
| 2003/0196283 A1 | 10/2003 | Eliav et al. | EP | 1 080 664 | 3/2001 | |
| 2003/0229959 A1 | 12/2003 | Gavney, Jr. et al. | EP | 0 870 440 B1 | 12/2001 | |
| 2004/0010869 A1 | 1/2004 | Fattori et al. | EP | 1 449 496 B1 | 9/2008 | |
| 2004/0016067 A1 | 1/2004 | Kraemer | FR | 459 442 | 11/1913 | |
| 2004/0025275 A1 | 2/2004 | Moskovich et al. | FR | 936529 | 6/1948 | |
| 2004/0060132 A1 | 4/2004 | Gatzemeyer et al. | FR | 1075171 | 10/1954 | |
| 2004/0060133 A1 | 4/2004 | Eliav | FR | 2541100 | 8/1984 | |
| 2004/0060137 A1 | 4/2004 | Eliav | FR | 2548528 | 1/1985 | |
| 2004/0068809 A1 | 4/2004 | Weng | FR | 2559361 | 8/1985 | |
| 2004/0083566 A1 | 5/2004 | Blaustein et al. | FR | 2 612 751 | 9/1988 | |
| 2004/0084063 A1 | 5/2004 | Vago et al. | FR | 2 616 306 | 12/1988 | |
| 2004/0103492 A1 | 6/2004 | Kwon et al. | FR | 2789887 | 2/1999 | |
| 2004/0123409 A1 | 7/2004 | Dickie | FR | 2 789 887 | 8/2000 | |
| 2004/0128784 A1 | 7/2004 | Ben-Ari | GB | 193 601 A | 3/1923 | |
| 2004/0168271 A1 | 9/2004 | McDougall | GB | 280067 | 11/1927 | |
| 2004/0177458 A1 | 9/2004 | Chan et al. | GB | 378129 A | 8/1932 | |
| 2004/0177462 A1 | 9/2004 | Brown, Jr. et al. | GB | 490892 | 8/1938 | |
| 2004/0221409 A1 | 11/2004 | Gavney, Jr. | GB | 690 422 A | 4/1953 | |
| 2004/0231076 A1 | 11/2004 | Gavney, Jr. | GB | 1164597 A | 9/1969 | |
| 2004/0231082 A1 | 11/2004 | Gavney, Jr. | GB | 1 325 860 A | 8/1973 | |
| 2004/0237236 A1 | 12/2004 | Gavney, Jr. | GB | 1 537 526 | 12/1978 | |
| 2004/0261203 A1 | 12/2004 | Dworzan | GB | 2137080 | 10/1984 | |
| 2005/0015901 A1 | 1/2005 | Gavney, Jr. | GB | 2 214 420 A | 9/1989 | |
| 2005/0060822 A1 | 3/2005 | Chenvainu et al. | GB | 2247297 | 2/1992 | |
| 2005/0060826 A1 | 3/2005 | Gavney | GB | 2 354 432 A | 3/2001 | |
| 2005/0115904 A1 | 6/2005 | Heikkila et al. | GB | 2 371 217 | 7/2002 | |
| 2005/0155172 A1 | 7/2005 | Gavney, Jr. et al. | JP | 50-11769 | 2/1975 | |
| 2005/0160546 A1 | 7/2005 | Weihrauch et al. | JP | 51-056165 U | 5/1976 | |
| 2005/0235439 A1 | 10/2005 | Braun et al. | JP | 52-125962 U | 9/1977 | |
| 2005/0273961 A1 | 12/2005 | Moskovich et al. | JP | 55-122633 U | 9/1980 | |
| 2006/0064833 A1 | 3/2006 | Jacobs | JP | 58-091931 U | 6/1983 | |
| 2006/0080799 A1 | 4/2006 | Lucente | JP | 59-066433 U | 5/1984 | |
| 2006/0162108 A1 | 7/2006 | Georgi et al. | JP | 61-198531 U | 11/1986 | |
| 2006/0272112 A9 | 12/2006 | Braun et al. | JP | 63-066928 U | 5/1988 | |
| 2007/0039113 A1 | 2/2007 | Kwon et al. | JP | 1-72128 | 5/1989 | |
| 2007/0056128 A1 | 3/2007 | Hohlbein et al. | JP | 2-119031 | 7/1990 | |
| 2007/0101530 A1 | 5/2007 | Furumoto | JP | 2-180203 | 7/1990 | |
| 2007/0169295 A1 | 7/2007 | Winter et al. | JP | 3-3226 | 1/1991 | |
| 2007/0204413 A1 | 9/2007 | Kuznetsov et al. | JP | 3-312978 | 9/1991 | |
| 2007/0251040 A1 | 11/2007 | Braun et al. | JP | 4-128627 | 11/1992 | |
| 2008/0060155 A1 | 3/2008 | Braun et al. | JP | 5-69342 | 3/1993 | |
| 2011/0271474 A1 | 11/2011 | Brown, Jr. et al. | JP | 576416 | 3/1993 | |
| | | | JP | 05096597 | 4/1993 | |

FOREIGN PATENT DOCUMENTS

| | | | | | |
|---|---|---|---|---|---|
| JP | 5-123222 | 5/1993 | | | |
| CA | 454913 | 3/1949 | JP | 6-327517 A2 | 11/1994 |
| CA | 2483825 | 10/2004 | JP | 08103326 | 4/1996 |
| CH | 103194 | 1/1924 | JP | 08103332 | 4/1996 |
| CH | 169312 | 5/1934 | JP | 61-90877 | 5/1996 |
| CH | 609238 | 2/1979 | JP | 08257043 | 8/1996 |
| DE | 558 852 | 9/1932 | JP | 08299372 | 11/1996 |
| DE | 813 990 | 7/1949 | JP | 9-140456 | 3/1997 |
| DE | 1 883 020 | 11/1963 | JP | 9-187319 A2 | 7/1997 |
| DE | 1210409 | 2/1966 | JP | 2000-157338 | 6/2000 |
| DE | 7343826 U | 11/1974 | JP | 2000-300345 | 10/2000 |
| DE | 2 402 785 | 7/1975 | JP | 2000-300347 | 10/2000 |
| DE | 75 33 143 U | 2/1976 | JP | 2000-308524 | 11/2000 |
| DE | 25 00132 A1 | 7/1976 | JP | 2001-190333 | 7/2001 |
| DE | 25 46 712 A1 | 4/1977 | JP | 2001-507360 | 7/2001 |
| DE | 2715414 A1 | 10/1978 | JP | 2002-010832 | 1/2002 |
| DE | 82 15 266.7 U1 | 9/1982 | JP | 2002-248118 | 9/2002 |
| DE | 3116189 A1 | 12/1982 | JP | 200361986 | 3/2003 |
| DE | 35 29 953 A1 | 3/1987 | JP | 2003093415 | 4/2003 |
| DE | 3628722 A1 * | 2/1988 | JP | 2003164473 | 6/2003 |
| DE | 37 44 630 A1 | 7/1989 | RU | 2045216 | 10/1995 |
| DE | 3928919 | 3/1991 | SU | 1687243 | 10/1991 |
| DE | 42 07 968 | 9/1993 | SU | 1752336 | 8/1992 |
| DE | 94 00 231.2 U1 | 3/1994 | WO | WO 91/05088 | 4/1991 |
| DE | 4412301 | 10/1995 | WO | WO 92/04589 | 3/1992 |
| DE | 19817704 | 10/1999 | WO | WO 93/24034 | 12/1993 |
| DE | 29919053 U1 | 12/2000 | WO | WO 95/01113 | 1/1995 |
| DE | 100 28 530 A1 | 12/2001 | WO | WO 96/15696 | 5/1996 |
| DK | 0076598 | 11/1953 | WO | WO 96/23431 | 8/1996 |
| EP | 0 189 816 A2 | 8/1986 | WO | WO 96/28994 | 9/1996 |
| EP | 0322562 | 5/1989 | WO | WO 97/14330 | 4/1997 |
| EP | 0 360 766 A1 | 3/1990 | WO | WO 98/01055 | 1/1998 |
| EP | 0 704 179 A1 | 4/1996 | WO | WO 98/18364 | 5/1998 |
| EP | 0 857 026 B1 | 1/2000 | WO | WO 99/37181 | 7/1999 |
| EP | 0 972 464 A1 | 1/2000 | WO | WO 00/21406 | 4/2000 |

| WO | WO 00/30495 | 6/2000 |
| --- | --- | --- |
| WO | WO 00/34022 | 6/2000 |
| WO | WO 00/47083 | 8/2000 |
| WO | WO 00/64307 | 11/2000 |
| WO | WO 00/76369 A2 | 12/2000 |
| WO | WO 01/06947 | 1/2001 |
| WO | WO 01/06946 | 2/2001 |
| WO | WO 01/21036 A1 | 3/2001 |
| WO | WO 01/43586 | 6/2001 |
| WO | WO 01/87101 A2 | 11/2001 |
| WO | WO 0189344 | 11/2001 |
| WO | WO 02/05679 A1 | 1/2002 |
| WO | WO 02/11583 | 2/2002 |
| WO | WO 02/19942 A1 | 3/2002 |
| WO | WO 02/38004 | 5/2002 |
| WO | WO 02/45617 | 6/2002 |
| WO | WO 03/015575 | 2/2003 |
| WO | WO 03/086140 A1 | 10/2003 |
| WO | WO 2004/014181 A1 | 2/2004 |

OTHER PUBLICATIONS

Board Opinion from the Chinese Patent Office with regard to Application No. 01806615.1 dated Jul. 17, 2007 with translation.
"Santroprene Rubber Physical Properties Guide, Tensile Properties, Dynamic Mechanical Properties, Tension and Compression Set, Fatigue Resistance", Advanced Elastomer Systems, pp. 2-19, Undated.
"Distinctive Plastics—Multi-Component Molding" http://www.distinctiveplastics.com/html/?id=2 copyright 2006.
Office Action for U.S. Appl. No. 10/389,448 dated Feb. 25, 2009; Braun et al.; filed Mar. 14, 2003.
Office Action for U.S. Appl. No. 10/389,448 dated Jun. 2, 2006; Braun et al.; filed Mar. 14, 2003.
Office Action for U.S. Appl. No. 10/389,448 dated Oct. 26, 2007; Braun et al.; filed Mar. 14, 2003.
Office Action for U.S. Appl. No. 10/389,448 dated Jul. 2, 2008; Braun et al.; filed Mar. 14, 2003.
Office Action for U.S. Appl. No. 10/389,448 dated Apr. 4, 2008; Braun et al.; filed Mar. 14, 2003.
Office Action for U.S. Appl. No. 10/389,448 dated Feb. 22, 2007; Braun et al.; filed Mar. 14, 2003.
Office Action for U.S. Appl. No. 11/825,387 dated Feb. 19, 2010; Braun et al.; filed Jul. 6, 2007.
Office Action for U.S. Appl. No. 11/825,387 dated Feb. 11, 2009; Braun et al.; filed Jul. 6, 2007.
Office Action for U.S. Appl. No. 11/825,387 dated Aug. 29, 2008; Braun et al.; filed Jul. 6, 2007.
Office Action for U.S. Appl. No. 11/825,387 dated Dec. 6, 2007; Braun et al.; filed Jul. 6, 2007.
Office Action for U.S. Appl. No. 12/186,639 dated Jun. 22, 2010; Braun et al.; filed Aug. 6, 2008.
Office Action for U.S. Appl. No. 12/186,639 dated Dec. 23, 2009; Braun et al.; filed Aug. 6, 2008
Office Action for U.S. Appl. No. 10/830,693 dated Feb. 26, 2009; Masterman et al.; filed Apr. 23, 2004.
Office Action for U.S. Appl. No. 10/830,693 dated Jul. 2, 2008; Masterman et al.; filed Apr. 23, 2004.
Office Action for U.S. Appl. No. 10/830,693 dated Mar. 3, 2008; Masterman et al.; filed Apr. 23, 2004.
Office Action for U.S. Appl. No. 10/830,693 dated Oct. 24, 2007; Masterman et al.; filed Apr. 23, 2004.
Office Action for U.S. Appl. No. 10/830,693 dated May 15, 2007; Masterman et al.; filed Apr. 23, 2004.
Office Action for U.S. Appl. No. 10/830,693 dated Aug. 17, 2006; Masterman et al.; filed Apr. 23, 2004.
Office Action for U.S. Appl. No. 11/799,793 dated Jun. 19, 2009; Braun et al.; filed May 2, 2007.
Office Action for U.S. Appl. No. 11/799,793 dated Apr. 25, 2008; Braun et al.; filed May 2, 2007.
Office Action for U.S. Appl. No. 10/820,562 dated Jun. 22, 2010; Braun et al.; Mar. 16, 2000.
Office Action for U.S. Appl. No. 10/820,562 dated Dec. 2, 2008; Braun et al.; filed Mar. 16, 2000.
Office Action for U.S. Appl. No. 10/820,562 dated Jul. 27, 2009; Braun et al.; filed Mar. 16, 2000.
Office Action for U.S. Appl. No. 10/820,562 dated Jul. 5, 2007; Braun et al.; filed Mar. 16, 2000.
Office Action for U.S. Appl. No. 10/820,562 dated May 8, 2006; Braun et al.; filed Mar. 16, 2000.
Office Action for U.S. Appl. No. 10/820,562 dated Aug. 15, 2005; Braun et al.; filed Mar. 16, 2000.
U.S. Appl. No. 10/820,562, filed Mar. 16, 2000, Braun et al.
U.S. Appl. No. 11/825,387, filed Jul. 6, 2007, Braun et al.
U.S. Appl. No. 12/186,639, filed Aug. 6, 2008, Braun et al.
"Plastics-Determination of flexural properties", British Standard, BS EN ISO 178:2003, Apr. 9, 2003.
Plastics Extrusion Technology Handbook Chapter Seven, Coextrusion and Dual-Extrusion Technology, pp. 168-189.
Modern Plastic Encyclopedia, 67:168-175, 1990.
Pebax 3533 SA 00, "Base Polymer for Structural Hot Melt Adhesives".
Product Literature, Kraton Polymers, pp. 13-21.
"Standard Test Methods for Flexural Properties of Unreinforced and Reinforced Plastics and Electrical Insulating Materials [Metric]", American Society for Testing Materials, Designation: D790M-93 Metric, pp. 1-9, Undated.
"Standard Terminology Relating to Plastics", American Society for Testing Materials, Designation: D883-00, pp. 1-15, Undated.
Hendricks et al., "Rubber-Related Polymers I. Thermoplastic Elastomers", Rubber Technology, pp. 515-533, Undated.
European Search Report dated Dec. 1, 2005.
U.S. Appl. No. 12/828,653, filed Jul. 1, 2010, Braun et al.
U.S. Appl. No. 12/828,667, filed Jul. 1, 2010, Braun et al.
All Office Actions, U.S. Appl. No. 09/526,679.
All Office Actions, U.S. Appl. No. 10/820,562.
All Office Actions, U.S. Appl. No. 11/825,387.
All Office Actions, U.S. Appl. No. 12/186,639.
All Office Actions, U.S. Appl. No. 12/828,653.
All Office Actions, U.S. Appl. No. 12/828,667.
All Office Actions, U.S. Appl. No. 13/154,644.

* cited by examiner

FIG. 8
FIG. 9
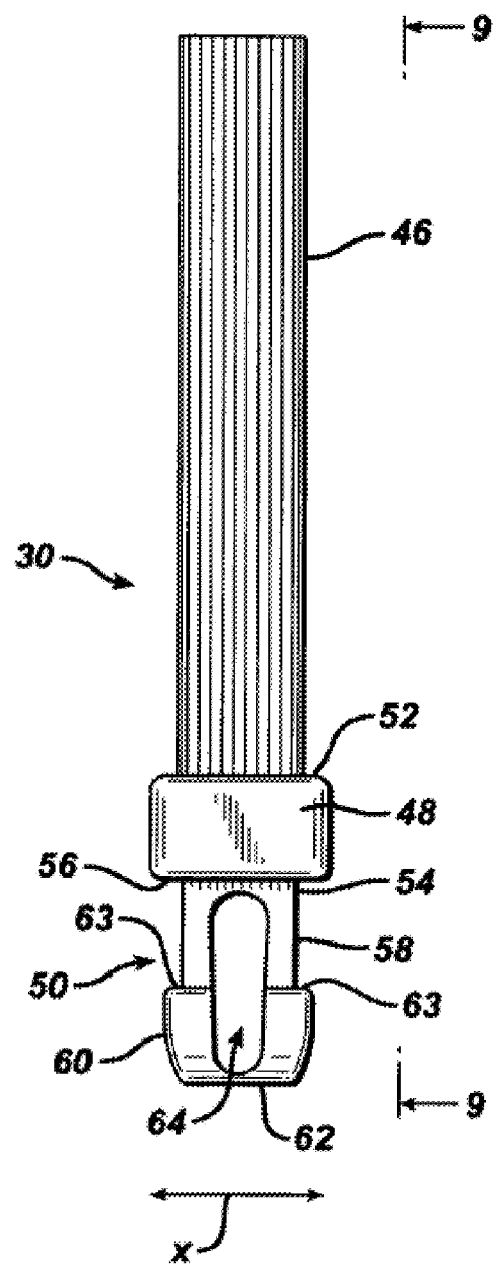
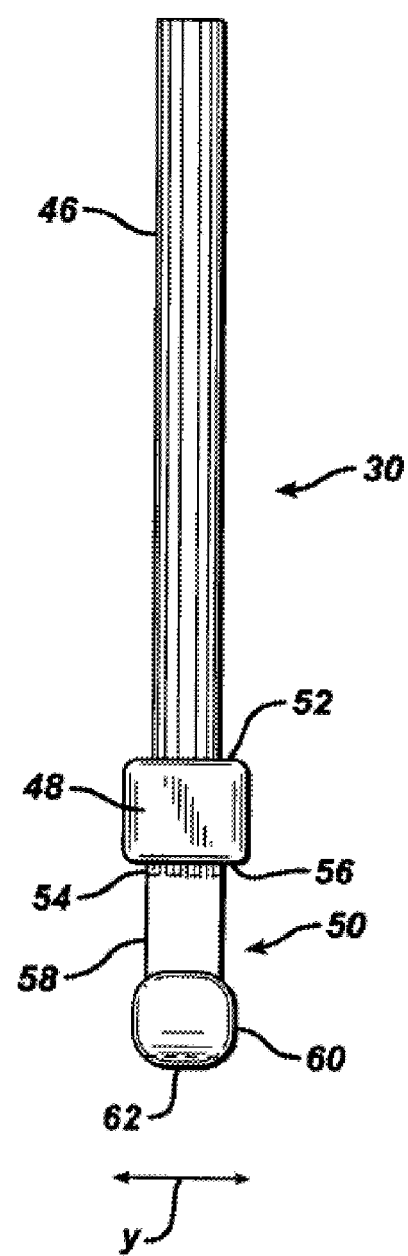

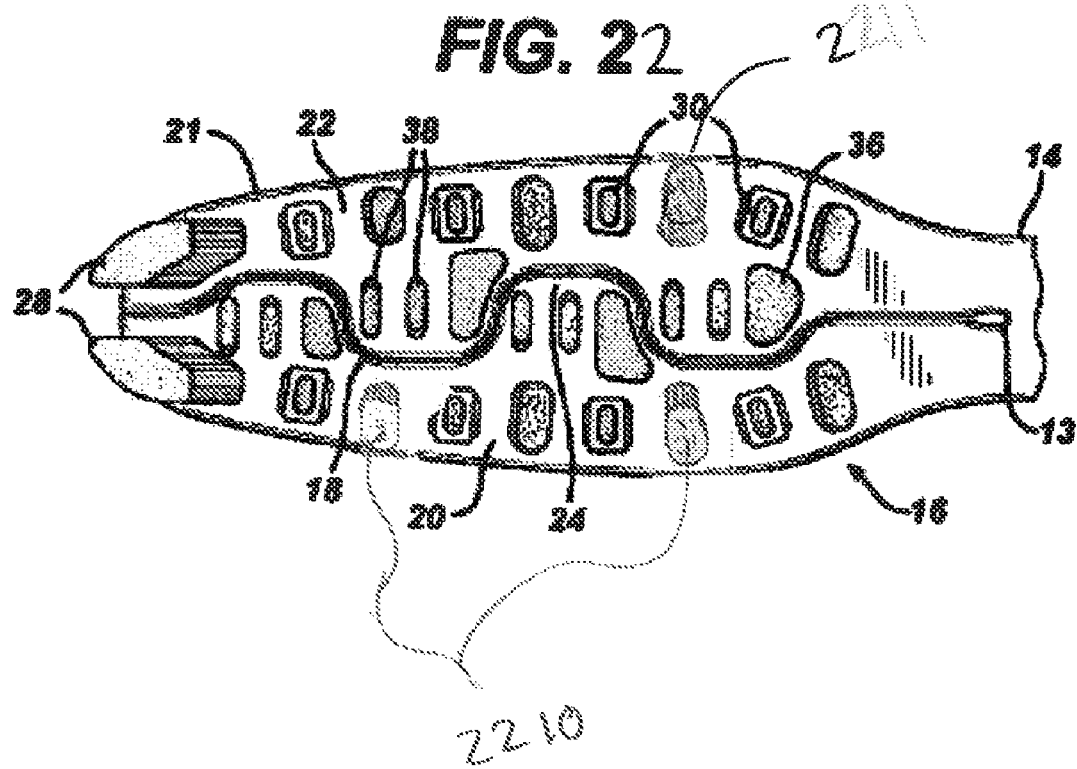

VIBRATING TOOTHBRUSH

CROSS-REFERENCE

This application is a continuation of U.S. patent application Ser. No. 10/830,693, filed on Apr. 23, 2004 and published as U.S. Patent Application Publication No. 2006/0272112, which is incorporated herein by reference.

FIELD OF THE INVENTION

The invention relates generally to the field of oral care, and in particular to toothbrushes. More specifically, the invention relates to a toothbrush that vibrates.

BACKGROUND OF THE INVENTION

U.S. Pat. No. 5,987,681 discloses an electric toothbrush with a handles a brush head and a shank which connects the handle to the brush head. A rotary motor is arranged in the handle and drives an unbalanced mass. The unbalanced mass driven by the motor is supported on one side or on both sides in the shank close to the brush head and is driven by an extended drive shaft, preferably an intermediate shaft, by the motor. When the motor is operated the toothbrush head vibrates.

The toothbrush disclosed in the '681 patent is typical of vibrating toothbrushes in that the features on the head of the toothbrush are fairly standard. For example, the bristles 21 on the head 2 are arranged in tufts lined up in straight rows and columns. The free ends of the bristles define a fairly flat surface. The vibrating aspect of the toothbrush has not been combined with any other more advanced head features to enhance cleaning of the oral cavity.

A Japanese patent document having an application number of 3-312978 discloses a toothbrush having a multiplicity of tufts of nylon bristles. In a first embodiment shown in FIGS. 1, 2 and 3 of the Japanese patent document, a plurality of cylindrical recessed sections in the head are set orthogonally to the longitudinal axial direction of a shank and are formed at equal intervals. Column-shaped rotary bodies 5 are respectively contained in the recessed sections. On the peripheral surfaces of the rotary bodies 5, along the axial direction, projected strip sections 5a are formed, and they are set in a state that they are positioned at the opening sections of the recessed sections. At the opening sections of the recessed sections, contact surfaces to be positioned on both the sides are formed. At both the ends of the upper surfaces of the projected strip sections 5a, nylon bristles 6 are arranged to be vertically erected.

As shown in FIG. 3, the arrangement described above allows bristles 6 to rotate during use of the brush. A problem with this brush is that two tufts of bristles are secured to each strip section 5a and thus must rotate in unison. As a result, an individual tuft of bristles cannot rotate independently of its "partner" tuft. The individual tuft may thus be prevented from achieving optimal penetration between two teeth during brushing because the partner tuft might contact the teeth in a different manner and interfere with rotation of the individual tuft.

FIGS. 4, 5 and 6 disclose a second embodiment in which each tuft of bristles is secured to the head by a ball and socket type arrangement. While this embodiment allows each tuft of bristles to swivel independent of the other tufts, it does have disadvantages. If a tuft of bristles is tilted out towards the side of the head and that tuft is positioned near the interface between the side and top surfaces of the teeth, chances are increased that the bristle tips will not even be in contact with the teeth during brushing. Further, the random orientation in which the tufts can end up after brushing detracts from the attractiveness of the brush.

The Japanese reference also discloses that the brush head is made of a unitary structure. As such, water cannot flow through any central portion of the brush head, thereby inhibiting the cleanability of the brush. Further, the unitary head structure does not allow different portions of the head to move independently of each other. Accordingly, the bristle tufts extending from the tuft cannot accommodate the varying tooth surfaces as well as a brush in which the head has two or more portions that can move or flex independent of each other.

SUMMARY OF THE INVENTION

A toothbrush constructed in accordance with the present invention may comprise a head extending from a neck which extends from a handle. The head includes a plurality of tooth cleaning elements extending therefrom. A first group of tooth cleaning elements can be located towards a free end of the head, and a second group of tooth cleaning elements can be located towards the outside of the head. A third group of tooth cleaning elements, which alternate with the second group of tufts, can be oriented at an acute angle to a top surface of the head in a direction that is across the width of the head. A fourth group of tooth cleaning elements can be located toward the inside of the head, and each of the fourth group of tooth cleaning elements can be made of a thermoplastic elastomer. Each of the fourth group of tooth cleaning elements can be in the shape of a curved wall. A fifth group of tooth cleaning elements can be located towards the inside of the head.

In another embodiment, a toothbrush comprises a head extending from a neck which extends from a handle. The head has a plurality of tooth cleaning elements extending therefrom. A first pair of tufts can be located towards a free end of the head, wherein each of the first pair of tufts may tilt away from the handle. A second group of cleaning elements may be made up of a thermoplastic elastomer and in the shape of a curved wall. Additionally, the toothbrush may further comprise a motor, a drive shaft projecting from the motor, and an eccentrically mounted weight secured to the drive shaft, wherein the rotating of the eccentrically mounted weight causes a vibration which is transmitted to the head and the tooth cleaning elements on the head.

BRIEF DESCRIPTION OF THE DRAWINGS

FIG. 8 is a front view of a pivoting tuft taken along the lines 8-8 of FIG. 13;

FIG. 9 is a side view of the pivoting tuft of FIG. 8 taken along lines 9-9;

FIG. 22 is a top view showing a toothbrush head constructed in accordance with the present invention.

DETAILED DESCRIPTION OF THE BEST MODE

Figure 5:
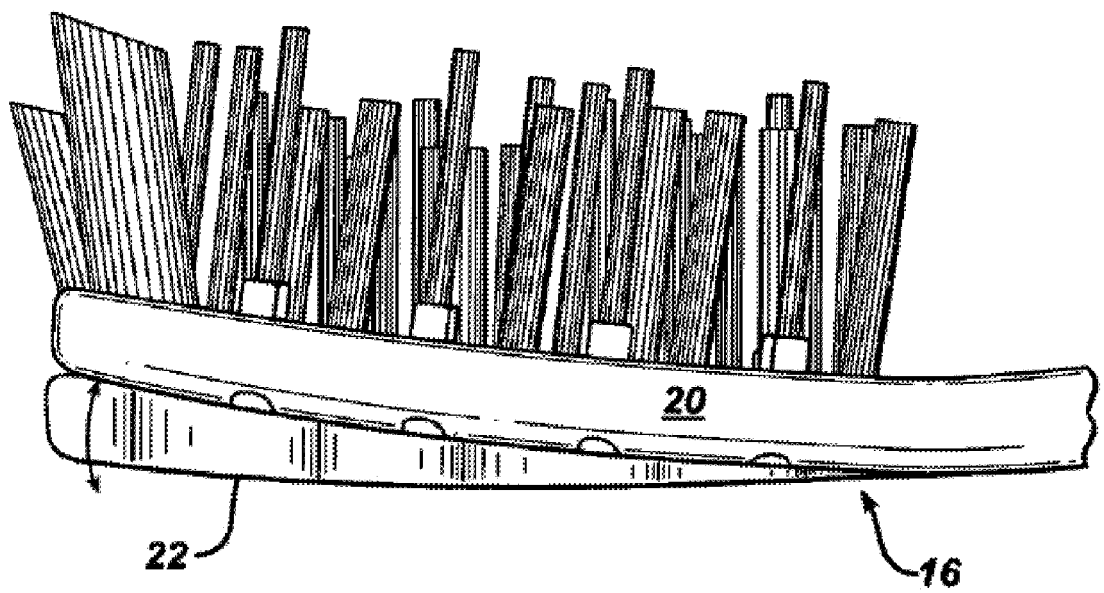
FIG. 5 is a side view of the head of FIG. 1 showing one of the head portions flexing.

Beginning with FIGS. 1-5, there is shown a toothbrush head 16 which extends from a neck 14 which extends from a handle (not shown) to form a toothbrush. The type of handle is not germane to the present invention. The head and handle are preferably made of polypropylene. The head has a serpentine split 18 which divides the head into two portions 20 and 22. An end of the split 13 near neck 14 is preferably circular in shape (see FIG. 2). As shown in FIG. 5, the split in the head allows portions 20 and 22 to flex or move independent of each other during use of the toothbrush, thus facilitating cleaning of the teeth.

Split 18 can also be defined as an opening in the head between head portions 20 and 22. This opening allows water to flow through the head, thereby enhancing cleaning of the top head surface which typically gets caked with toothpaste in spite of efforts to rinse the head clean.

Head portion 20 includes a projecting part 24 which fits (at least partially) into a recess 26 (see FIG. 6) defined by portion 22. Projecting part 24 has several tufts of bristles extending from it (to be described in further detail below) and is surrounded on three sides by head portion 22.

Figure 2:
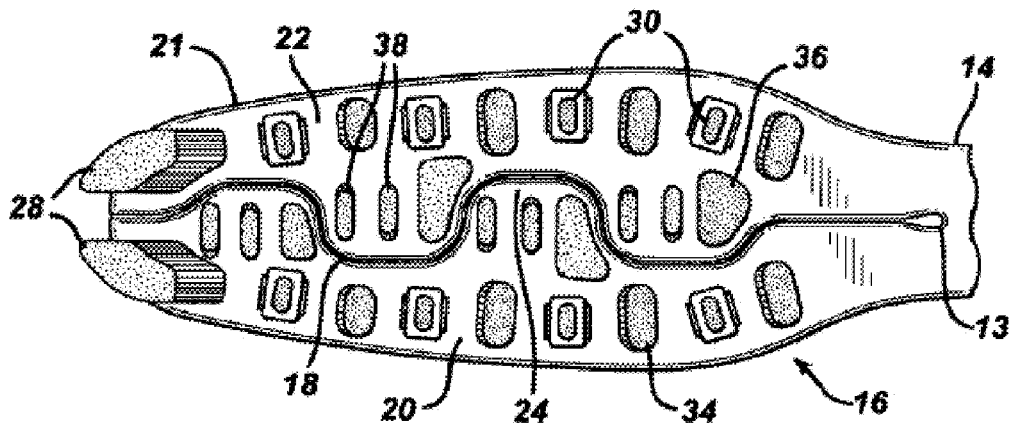
FIG. 2 is a top view of the head of FIG. 1.
Figure 3:
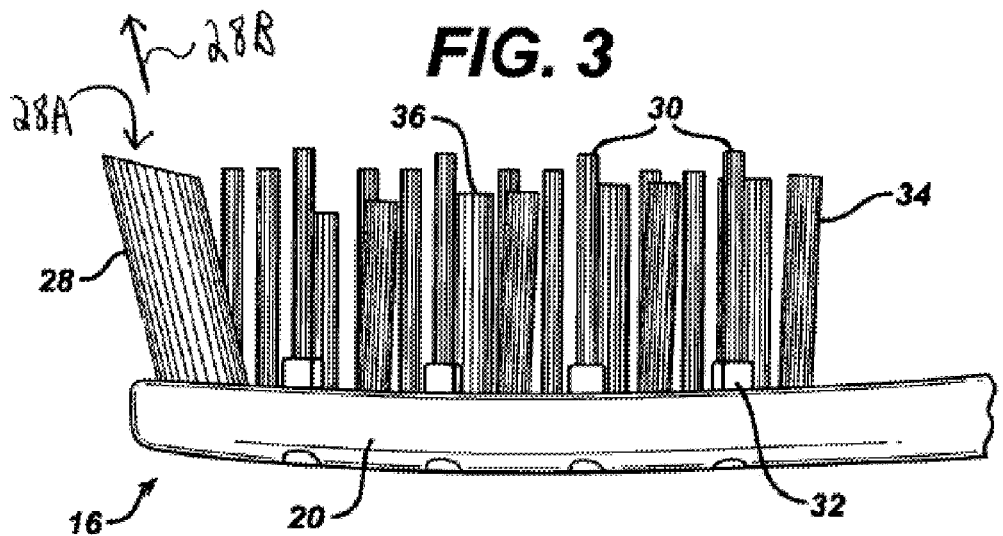
FIG. 3 is a side view of the head of FIG. 1.
Figure 4:
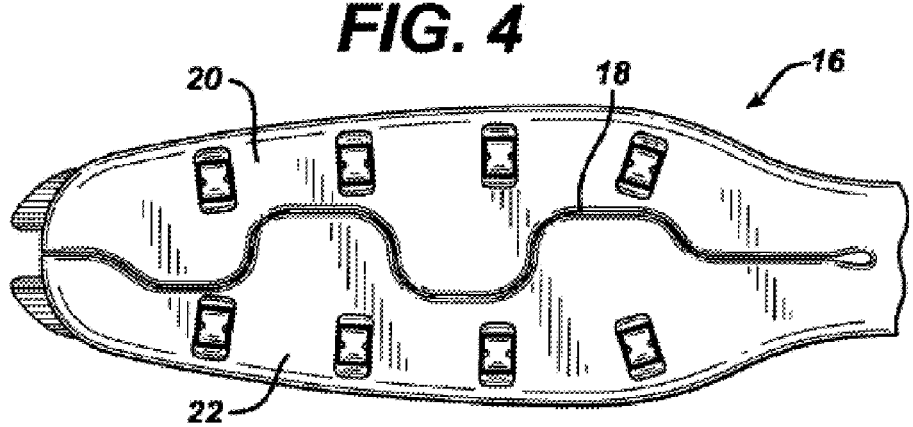
FIG. 4 is a bottom view of the head of FIG. 1.

Referring now to FIGS. 2 and 3, each of the tufts of bristles (tooth cleaning elements) on head 16 will be described. A first pair of tufts 28 are located towards the free end of the head, one on each head portion 20, 22. Each tuft has bristles (tooth cleaners) which preferably are each made of polybutyleneterepthalate (PBT) and have a diameter of 0.007 inches. The shortest bristles in tuft 28 have a length of 0.420 inches with the remaining bristles increasing in length steadily to a tip of the tuft. Each tuft tilts away from the handle by an angle of preferably about 12 degrees relative to that portion of the surface of the head from which it projects. As shown in FIG. 2, tufts 28 have a larger cross-section than any other tuft on the head.

A second group of tufts are pivoting tufts 30 (the only tufts on the head which are rotatable). There are four tufts 30 on each head portion 20, 22 which are located towards the outside of the head. Each tuft 30 can pivot up to about 15 degrees to either side of a vertical position on the head, more preferably being able to pivot up to about 8 degrees to either side of a vertical position on the head. The pivoting of tufts 30 is roughly towards or away from neck 14. Each tuft 30 includes a base support 32 made of polypropylene. The bristles are made of polyamide 6.12, have a diameter of 0.008 inches and extend 0.420 inches above the base support.

A third group of tufts 34 extend perpendicular to the head. There are four tufts 34 on each head portion 20, 22 which alternate with tufts 30. When viewed from the top (FIG. 2) the tufts are oval in shape (similar to tufts 30 but larger). In other words, the tufts 34 and 30 have oval shaped cross-sections. Each tuft 34 has bristles which are made of polyamide 6.12, have a diameter of 0.006 inches and extend above the head by about 0.385 inches.

A fourth group of tufts 36 are located towards the inside of the head. There are two such tufts on each head portion 20, 22. Each tuft 36 extends perpendicular to the head. The bristles of tuft 36 have a diameter of 0.006 inches, are made of polyamide 6.12 and rise about 0.360 inches above the head.

A fifth and final group of tufts 38 are also located towards the inside of the head (away from a perimeter 21 of the head). There are 4 pairs of tufts 38. In each pair one tuft is closer to neck 14 than the other tuft. In each pair of tufts 38, (a) a base of one tuft is closer to a first side of the head and this one tuft leans towards a second side of the head, and (b) a base of the other tuft is closer to the second side of the head and this other tuft leans towards the first side of the head. As such, the tufts in each pair lean across each other. The angle of tilt towards the side of the head is about five degrees. Each tuft 38 bristles which are made of PBT, have a bristle diameter of about 0.007 inches and extend about 0.460 inches above head 16. Each tuft 38 has an oval cross-section with a long dimension of the oval being oriented in the direction of tilt.

The bristles used on the head can be crimped (see U.S. Pat. No. 6,058,541) or notched (see U.S. Pat. No. 6,018,840). Other types of tooth cleaners besides bristles can be used. For example, a tuft of bristles could be replaced by an elastomeric fin. The US patents listed in this paragraph are incorporated herein by reference.

Figure 6:
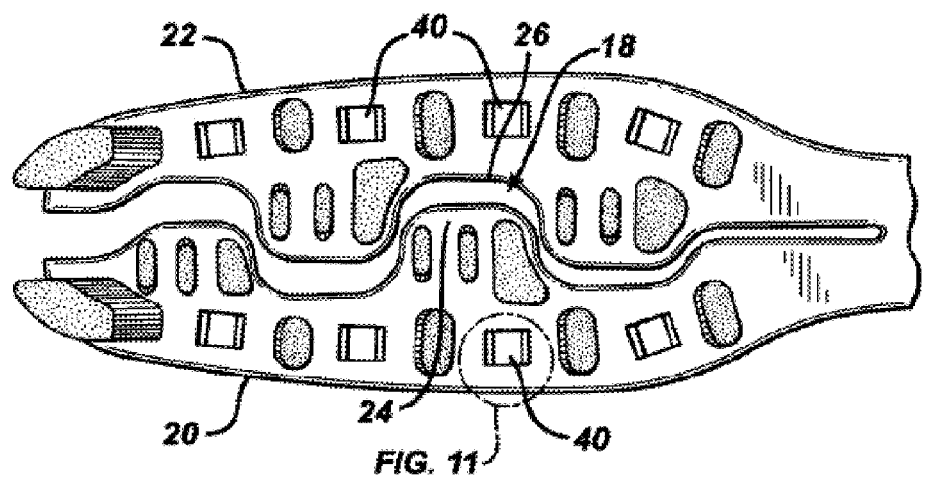
FIG. 6 is a top view of the head of FIG. 1 with the two head portions separated from each other.

Turning now to FIG. 6, a description will now be provided as to how the toothbrush (head) is made. In a first step, the head, neck and handle of the toothbrush are injection molded in a mold. During this injection molding step, tufts 28, 34, 36 and 38 are secured in the head by a hot-tufting process. Hot-tufting processes are notoriously well known by those skilled in the art (see e.g. U.S. Pat. Nos. 4,635,313; and 6,361,120; British patent application 2,330,791; and European patent application 676,268 A1).

Briefly, hot-tufting involves presenting ends of a multiplicity of groups of plastic filaments into a mold. Each group of filament ends inside the mold is optionally melted into a blob. Each filament group is cut to a desired length (either before or after being introduced into the mold) to form a tuft of bristles. The mold is closed and molten plastic is injected into the mold. When the plastic solidifies, it locks one end of the tufts of bristles into the head of the toothbrush.

It can be seen in FIG. 6 that the opening 18 between head portions 20 and 22 is much wider at this point than in the heads final form (see FIG. 2). In other words, head portions 20 and 22 are spaced a predetermined distance (preferably at least about 1 mm) from each other. Further, through holes 40 are created during the molding step for receiving pivoting tufts 30 at a later point in the manufacturing process. Holes 40 will be described in greater detail below.

Figure 7:
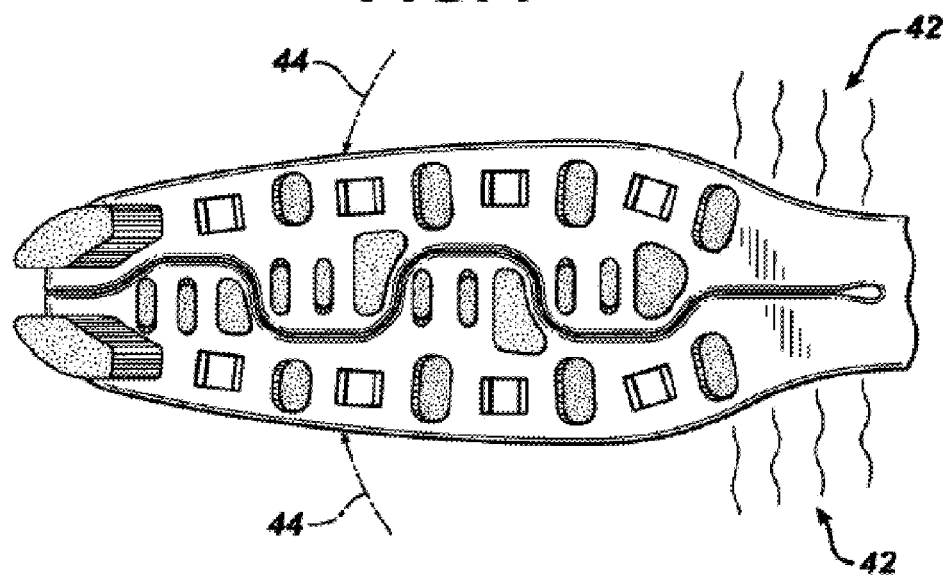
FIG. 7 is a top view of the head of FIG. 1 after the head portions have been positioned closer to each other.

With reference to FIG. 7, after the toothbrush is removed from the mold, heat 42 is applied to the head near the neck and to part of the neck (hereinafter the neck). The heat can be applied in a number of ways including hot air, radiant heating, ultrasonic or convection (e.g. hot oil) heating. Here the heat is shown being applied to the sides of the neck. It is preferable to apply the heat to the top and bottom surface of the neck. The heat brings the plastic up to 1.0-1.12 times its glass transition temperature (when temperatures are measured in the Kelvin scale). The plastic should not be heated above 1.12 times its glass transition temperature in order to avoid damaging the plastic. More preferably, the plastic is heated to about 1.03-1.06 times its glass transition temperature (measured in degrees Kelvin). The glass transition temperature for polypropylene is about 100 degrees centigrade whereas the glass transition temperature for copolyester and polyurethane is about 65 degrees centigrade.

Pressure 44 is then applied to head portions 20, 22 to move the portions towards each other. Once head portions 20, 22 are in the position shown in FIG. 2, the heated portion of the head/neck is cooled by, for example, exposing the heated portion to a cold gas or liquid. If room temperature air is used to cool the neck, such air should be applied for about 20-25 seconds. This has the effect of forming the two head portions into their final positions.

In order to achieve short process times, the highest temperature heat source which will not damage the plastic should be used. If too hot a heat source is used and/or if the heat is applied for too long, the plastic can be damaged. If the heat source is not hot enough, the process will take too long and/or head portions 20, 22 will not remain in their final desired positions. If the head/neck are made of polypropylene and hot air is used to heat the neck, (a) the heated air should be at a temperature of about 170 degrees centigrade and should be applied to the neck for about 70 seconds, (b) the polypropylene should be raised to a temperature of about 140 degrees centigrade, and (c) a nozzle which applies the hot air to the neck should be about 10 mm from the neck.

If copolyester or polyurethane is used as the material for the head neck, (a) the heated air should be at a temperature of 250 degrees centigrade and should be applied to the neck for about 10 seconds, (b) the material should be raised to a temperature of preferably 95-100 degrees centigrade, and (c) a nozzle which applies the hot air to the neck should be about 15-20 mm from the neck.

Heating the respective materials above for the time indicated allows the material to be softened and mechanically bent into its final form. Exceeding the heating times above could cause the material to overheat and become damaged.

Turning to FIGS. 8 and 9, each pivoting tuft 30 has a multiplicity of bristles 46, a base support 48 and an anchor pivot 50. The bristles are secured to and extend from a first end 52 of the base support while a first end 54 of the anchor pivot extends from a second end 56 of the base support. The base support and anchor pivot are preferably a unitary structure made of the same material. Anchor pivot 50 includes a first portion 58 near the first end 54 and a second portion 60 near a second end 62 of the anchor pivot. First portion 58 is smaller in an X an Y dimension than second portion 60. Base support 48 is larger in an X and Y dimension than second portion 60 of the anchor support. Second portion 60 includes a pair of lips 63. The anchor pivot defines an opening 64 therethrough.

Tuft 30 can also be made by a hot-tufting type process as described above. Instead of injecting plastic into the mold to form a toothbrush handle, neck and head, the plastic is injected into a mold to form base support 48 and anchor pivot 50, capturing bristles 46 when the injected plastic cools.

Figure 10:
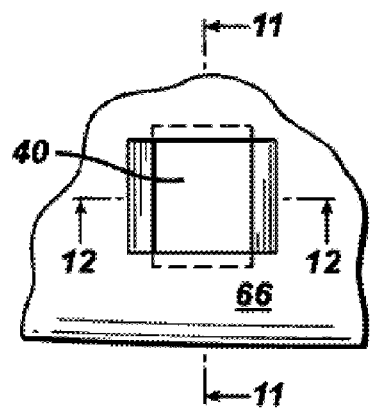
FIG. 10 is a top view of one of the holes in the head for receiving the pivoting tuft (see FIG. 6)
Figure 11:
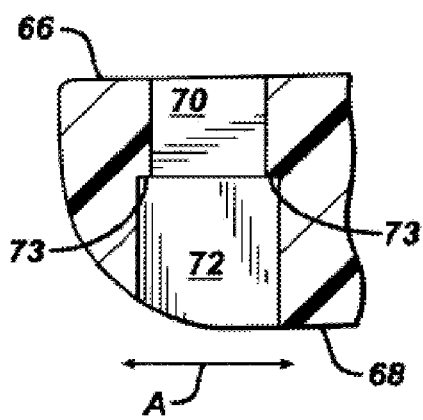
FIG. 11 is a sectional view of FIG. 10 taken along lines 11-11.
Figure 12:
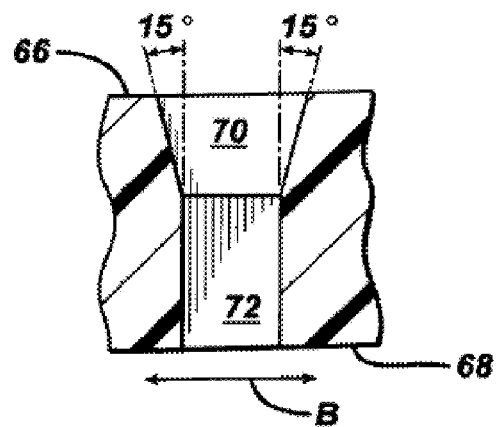
FIG. 12 is a sectional view of FIG. 10 taken along lines 12-12.

With reference to FIGS. 10-12, through holes 40 (FIG. 6) will now be described. Each hole 40 extends from a top surface 66 of the brush head through a bottom surface 68. Hole 40 includes first and second portions 70 and 72. Portion 72 is substantially a parallelepiped except that some of its lower section is rounded off (see FIG. 11). Portion 70 is also substantially a parallelepiped except that two of its sides are flared to the sides by about 15 degrees (see FIG. 12). Hole portion 72 is longer in a dimension A than hole portion 70 (FIG. 11). Hole portion 70 has about the same width in a dimension B as hole portion 72 where hole portions 70 and 72 meet (FIG. 12). Dimensions A and B are substantially perpendicular to each other in this embodiment. A pair of lips 73 are defined by this arrangement.

Figure 13:
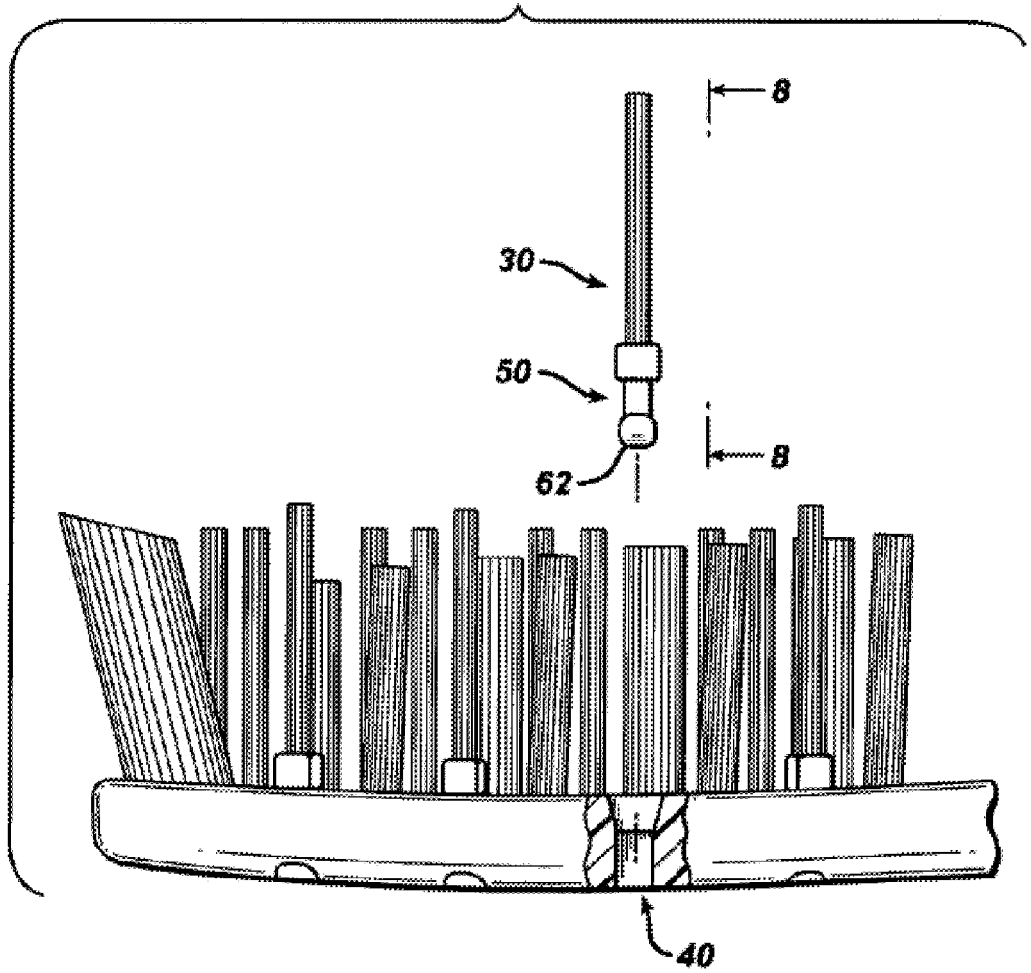
FIG. 13 is a side view of the head of FIG. 1 (a portion is removed to facilitate viewing) and a pivoting tuft prior to insertion into the head.
Figure 14:
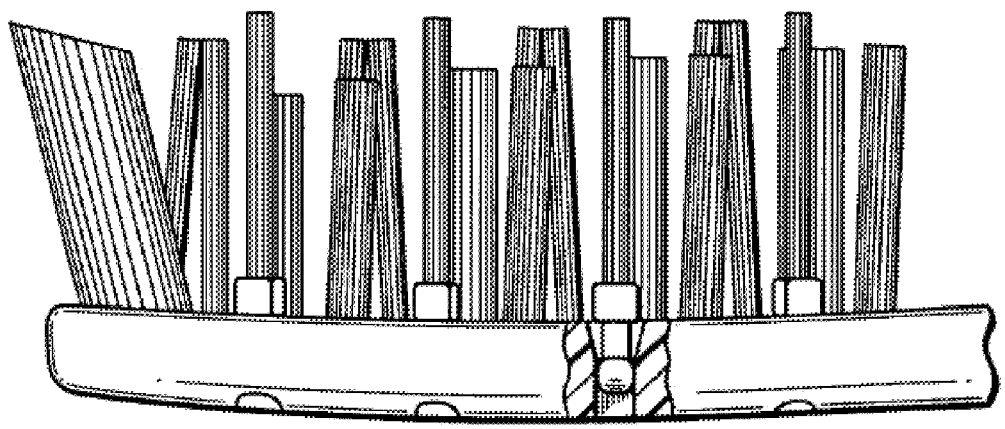
FIG. 14 is a side view of the head of FIG. 1 (a portion is removed to facilitate viewing) and a pivoting tuft after insertion into the head.

Turning now to FIGS. 13-16, the insertion of pivoting tufts 30 into holes 40 will be described. A tuft 30 is positioned over a hole 40 with end 62 of anchor pivot 50 facing the hole (FIG. 13). As shown in FIGS. 16A-C, tuft 30 is moved towards hole 40 until end 62 starts to enter the hole (FIG. 16A). Tuft 30 is then pressed into the hole causing sides of hole portion 70 to squeeze second portion 60 of the anchor pivot. Accordingly, anchor pivot 50 collapses causing opening 64 to become temporarily smaller. Tuft 30 is then pushed all the way into hole 40 (FIG. 16C) at which point the resilient plastic anchor pivot springs back to its form shown in FIG. 16A. This paragraph describes a snap-fit retention of tuft 30 to the head.

Figure 16A:
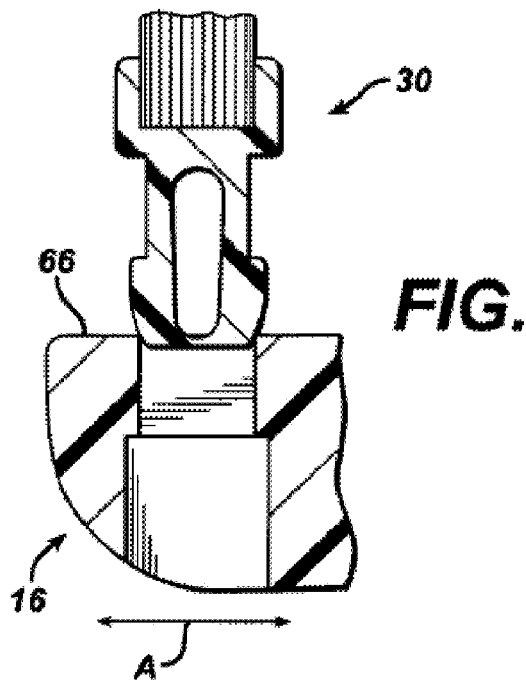
FIGS. 16A-C are sectional views of FIG. 15 taken along the lines 16A-C-16A-C.
Figure 16B:
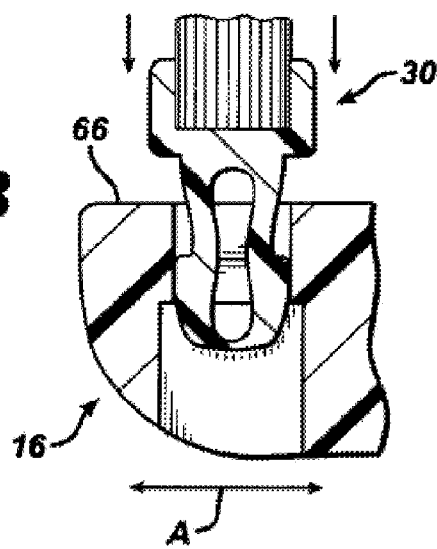
Figure 16C:
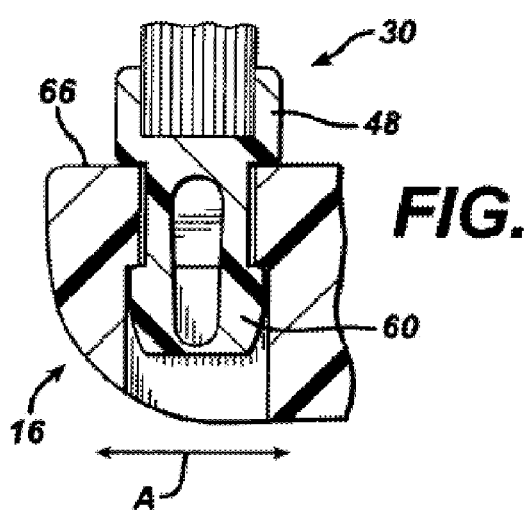

Referring to FIG. 16C, base support 48 is longer in the A dimension than hole portion 70 and thus prevents tuft 30 from being pressed further into hole 40. Second portion 60 is also longer in the A dimension than hole portion 70 and so prevents tuft 30 from moving back out of hole 40. This is due to the fact that lips 63 (FIG. 8) engage lips 73 (FIG. 11). This arrangement also prevents tuft 30 from rotating about the long axis of the bristles.

Figure 15:
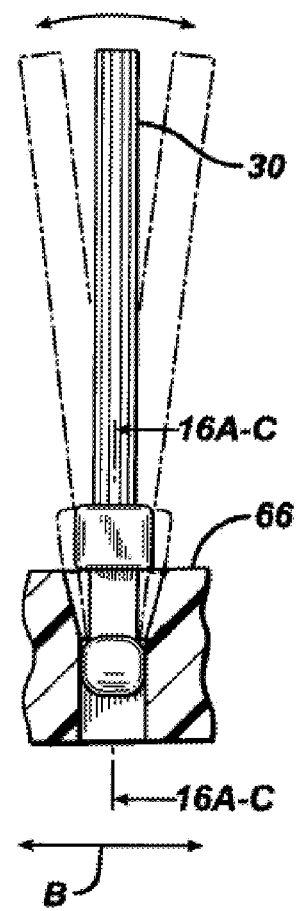
FIG. 15 is a side view of the pivoting tuft showing its motion.

As shown in FIG. 15, tuft 30 pivots when it is engaged by, for example, portions of the oral cavity during brushing. Preferably each tuft 30 can pivot up to about 15 degrees to either side of a position perpendicular to surface 66.

Figure 17:
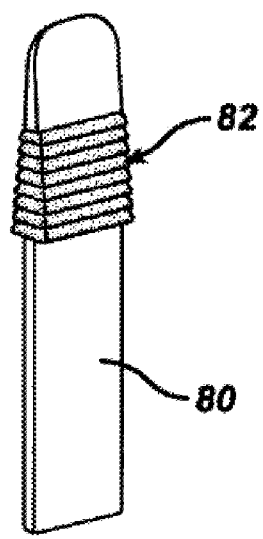
FIG. 17 is a perspective view of a tooth cleaner in the form of a ribbed fin.
Figure 18:
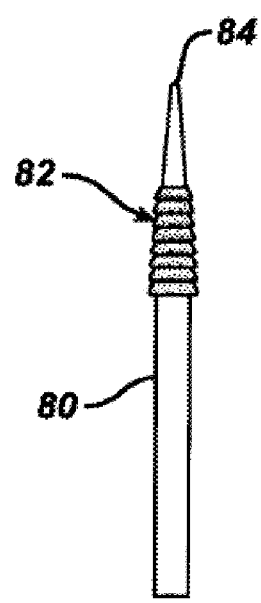
FIG. 18 is a side view of the ribbed fin of FIG. 17.

Turning to FIGS. 17 and 18, another type of tooth cleaning element in the form of a fin 80 is disclosed. Each fin is supported by a base support 48 and an anchor pivot 50 (both not shown) as described above, allowing the fin to pivot on the brush head. Alternatively, a fin can be securely affixed to the head so that it does not pivot. The fin is created of a thermoplastic elastomer (TPE) by an injection molding process. In this embodiment, a textured surface is provided by a series of ribs 82. These ribs enhance cleaning of the oral cavity. The ribs are formed by injection molding a TPE over the fin. The ribs are preferably softer than the fin. Alternative textured surfaces (e.g. dimples) can be used in place of the ribs.

As shown in FIG. 18, the fin has a width of preferably about 0.030 inches. The long dimension of the fin above the base support is preferably 0.420 inches. A tip 84 of fin 80 has a width of preferably 0.007 inches. The distance from the base of the ribs to tip 84 is about 0.168 inches whereas the distance from the top of the ribs to the tip is about 0.079 inches. The top of the ribs have a width of about 0.035 inches. The ribs (textured surface) preferably extend about 2-12 mil away from said fin.

Figure 1:
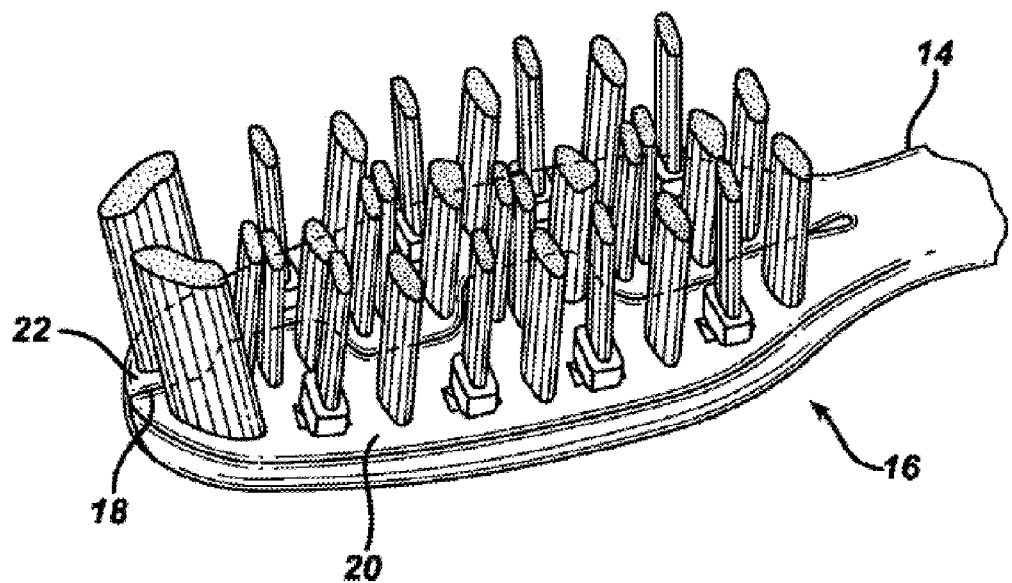
FIG. 1 is a perspective view of the toothbrush head of FIG. 1.
Figure 19:
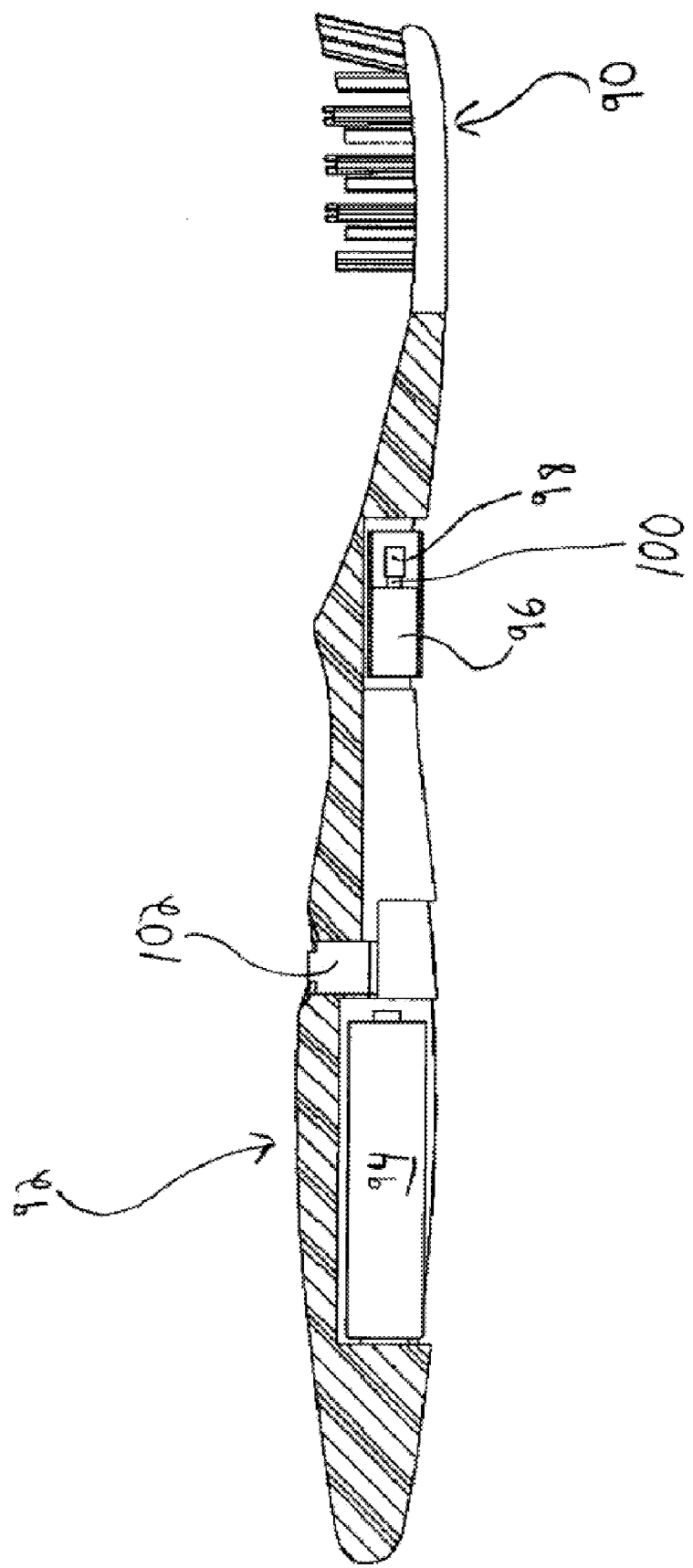
FIG. 19 is a side view in partial section of a toothbrush disclosing another embodiment of the invention.

FIG. 19 is a partial sectional view of a toothbrush showing another embodiment of the invention. A head 90 and all of the tooth cleaning elements projecting from the head are the same as shown in FIG. 1. A handle 92 encloses a 1.5 volt triple A battery 94 and a motor 96. An eccentrically mounted weight 98 is secured to a drive shaft 100 which projects from the motor. An on/off switch 102 projects slightly out of the handle.

When the on/off switch is depressed a first time, an electrical circuit between battery 94 and motor 96 is completed causing the motor to rotate shaft 100. The shaft preferably rotates at between about 9700-12,400 rpm. Weight 98 is thus also rotated. As the weight is eccentrically mounted, rotating the weight causes a vibration which is transmitted to handle 92, head 90 and the tooth cleaning elements on the head.

One type of motor which can be used is a P/N Q6DL-2.6A with a #17 counterweight attached. This motor was bought from Jin Long Machinery, 640 Dean Street, Brooklyn, N.Y. 11238 (718.783.2328). Also see www.vibratormotor.com.

It should be noted that tooth cleaning elements 28 (FIG. 3) are oriented at an acute angle relative to that portion of a top surface of head 16 from which elements 28 project. In another embodiment of the invention, one or more of tooth cleaning elements 34, 36 and 38 can also be oriented at an acute angle to the top surface of head 16. The tooth cleaning elements can be oriented at two or more different angles and can also be angled in different directions such as along the length of the head, across the width of the head or part way between the length and width of the head (a compound angle). The tooth cleaning elements are preferably at an angle of between about 65-85 degrees measured from a line parallel or tangent to the top surface of the head. Some examples of tooth cleaning elements 2210 oriented at an acute angle to the top surface of the head 16 are shown in FIG. 22.

All of tooth cleaning elements 28, 30, 34, 36 and 38 also have a non-circular cross-sections (see FIG. 2). Elements 30, 34 and 38 have cross-sections that can be described as a prolate ellipsoid with flattened long sides. Element 28 has a free end that defines a plane 28A which is non-perpendicular to a direction 28B in which element 28 extends away from head portion 20. The free end of element 28 can alternatively have a non-flat shape (e.g. curved) which can be formed by a hot tufting or spool feed tufting manufacturing process.

As shown in FIG. 3, the various tooth cleaning elements 28, 30, 34, 36 and 38 extend different heights above head 16. These elements also have several different cross-sections. In an alternative embodiment, the elements can also be at a number of different acute angles relative to the top surface of the head.

Figure 20:
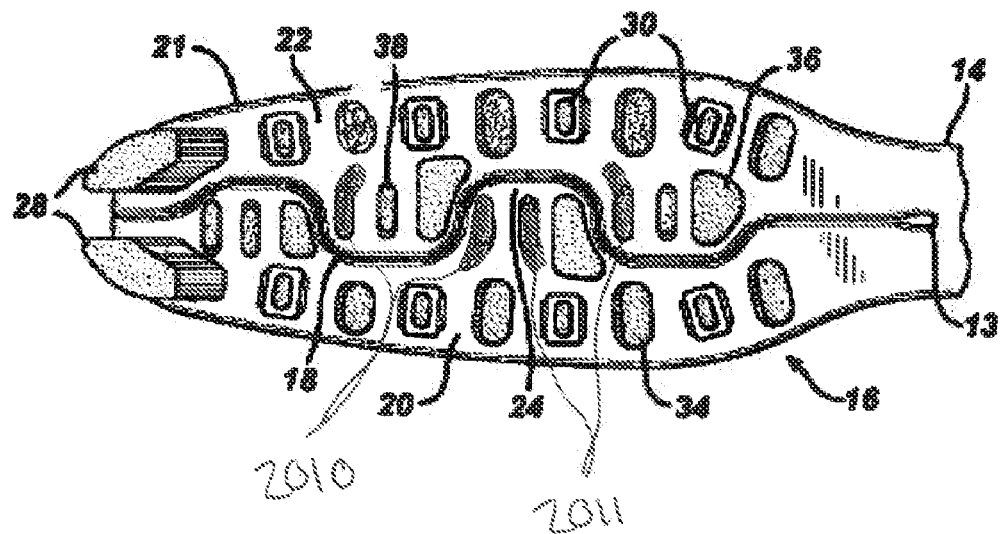
FIG. 20 is a top view showing a toothbrush head constructed in accordance with the present invention.

Further, one or more of these tooth cleaning elements can be replaced by a tooth cleaning element which is made of a thermoplastic elastomer. The thermoplastic elastomer tooth cleaning element can be a unitary structure, or it can be made up of a number of substructures. For example, the thermoplastic elastomer element could be a large unitary bristle (i.e. a nub) or it could have a number of smaller bristles (e.g. a tuft of bristles). The element could also be in the shape of a fin (as in FIG. 18), cup (e.g. prophy cup) or wall (curved or straight). Examples of curved walls 2010 and 2011 are shown in FIG. 20.

Figure 21:
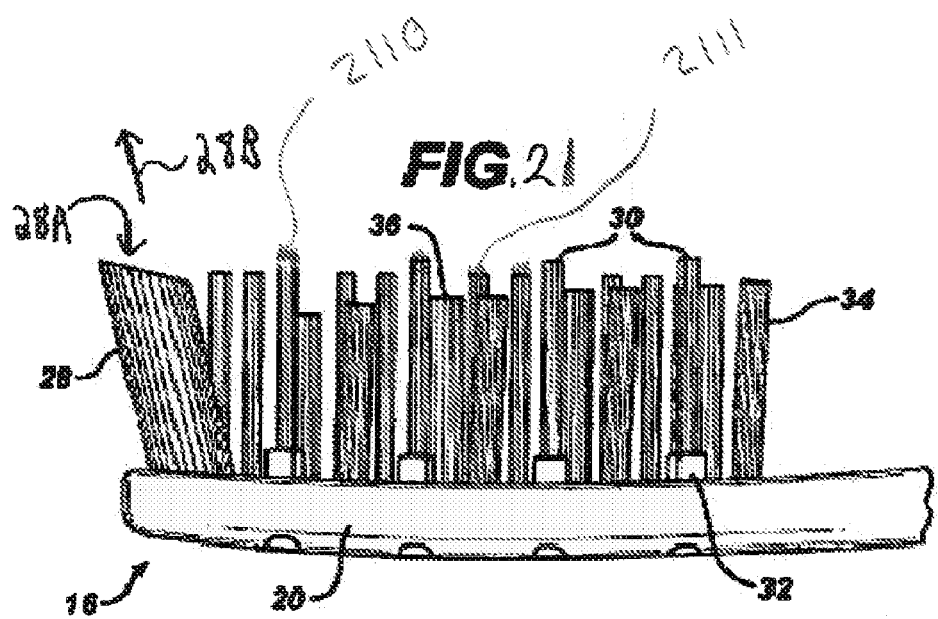
FIG. 21 is a side view showing a toothbrush head constructed in accordance with the present invention.

Different types of bristles which can be used on the toothbrush are bristles which (a) are tapered at their free end, (b) are flagged at their free end, (c) are hollow (see e.g. U.S. Pat. No. 5,836,769), (d) are crimped (see e.g. U.S. Pat. No. 6,058,541), (e) have a cross-shaped or triangular cross-section, (f) are flocked, or (g) are notched (see e.g. U.S. Pat. No. 6,018,840). Examples of tapered bristles 2110 and 2111 are shown in FIG. 21.

A tuft of bristles can alternatively have bristles made of different materials (e.g. some bristles made of nylon and other bristles made of polybutylene terepthalate) or bristles having different diameters.

Further, the plastic head can alternatively be covered partially or completely in a thermoplastic elastomer which acts to protect the teeth and gums from the plastic head. This results in a head made of two materials. Additional types of materials could also be provided on the head.

The invention has been described with reference to a preferred embodiment. However, it will be appreciated that variations and modifications can be effected by a person of ordinary skill in the art without departing from the scope of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush, comprising:
a head extending from a neck which extends from a handle, the head having a plurality of tooth cleaning elements extending therefrom, the head further comprising a top surface and a back surface opposite the top surface;
a longitudinal axis and a lateral axis, the lateral axis being perpendicular to the longitudinal axis, the lateral axis being generally parallel to the top surface of the head;
a first group of tooth cleaning elements located towards a free end of the head, each of the first group of tooth cleaning elements being tilted at an angle which is away from the handle, the first group of tooth cleaning elements having free ends which collectively define a plane which is non perpendicular to a direction in which the first group of tooth cleaning elements extend away from the head;
a second group of tooth cleaning elements located towards the outside of the head;
a third group of tooth cleaning elements which alternate with the second group of tooth cleaning elements, wherein the third group of tooth cleaning elements are oriented at an acute angle to a top surface of the head in a direction that is across the width of the head;
a fourth group of tooth cleaning elements made of a thermoplastic elastomer, wherein the fourth tooth group of tooth cleaning elements comprise a plurality of curved walls, and wherein at least one of the fourth group of tooth cleaning elements comprises a base portion and a cleaning portion, the base portion having a first part and a second part, the first part being disposed nearer to the top surface than the second part, the first part having a first length generally parallel to the longitudinal axis and the second part having a second length generally parallel to the longitudinal axis, wherein the second length is greater than the first length, and wherein the base portion comprises a distal end located furthest from the cleaning portion and inboard of the back surface such that the base support does not extend beyond the back surface;

a fifth group of tooth cleaning elements located towards the inside of the head; and an opening having an entrance in the top surface of the head, wherein the base portion of at least one of the fourth group of tooth cleaning elements is disposed in the opening, wherein the opening comprises a first portion, and a second portion, wherein the first portion is disposed adjacent the top surface and the second portion is disposed adjacent the back surface of the head, and wherein the first portion has a width which is shorter than the width of the second portion, the width being generally parallel to the lateral axis.

2. The toothbrush of claim 1 wherein at least one of the second group of tooth cleaning elements or the third group of tooth cleaning elements comprise tapered bristles.

3. The toothbrush of claim 1, wherein the toothbrush further comprises a vibration device.

4. The toothbrush of claim 3, wherein the vibration device is positioned closer to the free end of the head than an opposite end of the toothbrush.

5. The toothbrush of claim 3, wherein the vibration device comprises a motor, a drive shaft projecting from the motor, and an eccentrically mounted weight secured to the drive shaft.

6. The toothbrush of claim 5, wherein rotating the eccentrically mounted weight causes a vibration which is transmitted to the head and the tooth cleaning elements on the head.

7. The toothbrush of claim 1, wherein the fourth group of cleaning elements is a unitary structure.

8. The toothbrush of claim 1, wherein the fifth group of tooth cleaning elements are oriented at an acute angle to a top surface of the head in a direction that is across the width of the head.

9. The toothbrush of claim 1, wherein the fourth group of tooth cleaning elements are fixed to the head such that the fourth group of tooth cleaning elements does not rotate.

10. The toothbrush of claim 1, wherein the head is at least partially covered in a thermoplastic elastomer.

11. The toothbrush of claim 1, wherein the first portion has a first length at the entrance in the top surface and a second length at an interface between the first portion and the second portion meet, and wherein the first length is greater than the second length.

12. The toothbrush of claim 11, wherein second portion has a third length adjacent the back surface, wherein the third length is the same as the second length of the interface.

13. The toothbrush of claim 1, wherein none of the fourth group of tooth cleaning elements is rotatable.

14. The toothbrush of claim 1, wherein at least one of the fourth group of tooth cleaning elements is rotatable.

15. A toothbrush comprising:

a head extending from a neck which extends from a handle, the head having a plurality of tooth cleaning elements extending therefrom, the head further comprising a top surface and a back surface opposite the top surface;

a longitudinal axis and a lateral axis, the lateral axis being perpendicular to the longitudinal axis, the lateral axis being generally parallel to the top surface of the head;

a first pair of tufts located towards a free end of the head, each of the first pair of tufts tilting away from the handle;

a second group of cleaning elements are made up of a thermoplastic elastomer and in the shape of a curved wall, and wherein at least one of the second group of tooth cleaning elements comprises a base portion and a cleaning portion, the base portion having a first part and a second part, the first part being disposed nearer to the top surface than the second part, the first part having a first length generally parallel to the longitudinal axis and the second part having a second length generally parallel to the longitudinal axis, wherein the second length is greater than the first length, and wherein the base portion comprises a distal end located furthest from the cleaning portion and inboard of the back surface such that the base support does not extend beyond the back surface;

a motor, a drive shaft projecting from the motor, and an eccentrically mounted weight secured to the drive shaft, wherein the rotating of the eccentrically mounted weight causes a vibration which is transmitted to the head and the tooth cleaning elements on the head; and an opening having an entrance in a top surface of the head, wherein the base of at least one of the second group of cleaning elements is disposed in the opening, wherein the opening comprises a first portion, and a second portion, wherein the first portion is disposed adjacent the top surface and the second portion is disposed adjacent the back surface of the head, and wherein the first portion has a width which is shorter than the width of the second portion, the width being generally parallel to the lateral axis.

16. The toothbrush of claim 15, wherein the second group of cleaning elements are a unitary structure.

17. The toothbrush of claim 15, further comprising a third group of tufts which alternate with the second group of cleaning elements.

18. The toothbrush of claim 15, wherein the first pair of tufts are angled in different directions.

19. The toothbrush of claim 15, wherein the head is at least partially covered in a thermoplastic elastomer.

20. The toothbrush of claim 15, wherein the first portion has a first length at the entrance in the top surface and a second length at an interface between the first portion and the second portion meet, and wherein the first length is greater than the second length.

21. The toothbrush of claim 20, wherein second portion has a third length adjacent the back surface, wherein the third length is the same as the second length of the interface.

22. The toothbrush of claim 15, wherein none of the second group of tooth cleaning elements is rotatable.

23. The toothbrush of claim 15, wherein at least one of the second group of tooth cleaning elements is rotatable.

24. The toothbrush head of claim 15, wherein the plurality of elastomeric contact elements are unitary.

25. A toothbrush comprising the toothbrush head of claim 15, a neck, and a handle, wherein the neck extends between the handle and the head.

* * * * *